US009234653B2

(12) United States Patent
Ferguson

(10) Patent No.: US 9,234,653 B2
(45) Date of Patent: Jan. 12, 2016

(54) MEDICAL HEADLAMP OPTICAL ARRANGEMENT PERMITTING VARIABLE BEAM WIDTH

(71) Applicant: RIVER POINT, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days.

(21) Appl. No.: 14/243,263

(22) Filed: Apr. 2, 2014

(65) Prior Publication Data

US 2014/0334157 A1 Nov. 13, 2014

Related U.S. Application Data

(63) Continuation-in-part of application No. 13/972,489, filed on Aug. 21, 2013.

(60) Provisional application No. 61/822,493, filed on May 13, 2013.

(51) Int. Cl.

| | |
|---|---|
| ***A61B 1/06*** | (2006.01) |
| ***F21S 4/00*** | (2006.01) |
| ***F21V 5/00*** | (2015.01) |
| ***G02B 6/06*** | (2006.01) |
| ***F21S 8/00*** | (2006.01) |
| ***F21V 21/084*** | (2006.01) |
| ***F21V 11/10*** | (2006.01) |

(52) U.S. Cl.
CPC ............... *F21V 21/084* (2013.01); *F21V 11/10* (2013.01)

(58) Field of Classification Search
CPC ......... F21V 21/084; F21V 11/10; F21V 5/04; A61B 2019/262; A61B 19/5202; A61B 2019/521; A61B 1/06; A61B 1/227; A61B 1/0684; A61B 1/00032; F21L 15/16; B29C 70/72
USPC .......................................................... 362/572
See application file for complete search history.

(56) References Cited

U.S. PATENT DOCUMENTS 4,104,709 A * 8/1978 Kloots .......................... 362/105
4,596,449 A * 6/1986 Iwata et al. ................... 359/696
(Continued)

FOREIGN PATENT DOCUMENTS

KR 1020110095674 A1 8/2011

OTHER PUBLICATIONS

Medled, medLED Sapphire O.R. Surgical Headlight System, brochure, medLED//Portable Surgical Lighting, Portland, Oregon United States of America.

*Primary Examiner* — Evan Dzierzynski
*Assistant Examiner* — Erin Kryukova
(74) *Attorney, Agent, or Firm* — Timothy E. Siegel Patent Law, PLLC; Timothy E. Siegel

(57) ABSTRACT

A medical headlamp having a front from which light is selectively emitted. The headlamp includes a beam origination portion that produces a light beam and an iris assembly, positioned in front of the beam origination portion, having a user accessible actuator and an iris, responsive to the actuator to block a user-selectable portion of the light beam. The iris is also responsive to the actuator to block none of the light beam, for maximum efficiency, when a user so selects.

4 Claims, 4 Drawing Sheets

(56) References Cited

U.S. PATENT DOCUMENTS

| | | | | |
|---|---|---|---|---|
| 5,430,620 | A * | 7/1995 | Li et al. | 362/572 |
| 5,709,459 | A * | 1/1998 | Gourgouliatos et al. | 362/105 |
| 5,769,523 | A * | 6/1998 | Feinbloom | 362/554 |
| 5,774,271 | A * | 6/1998 | Lagerway et al. | 359/649 |
| 5,926,320 | A | 7/1999 | Parkyn, Jr. et al. | |
| 6,464,383 | B1 * | 10/2002 | Northington et al. | 362/572 |
| 7,210,810 | B1 | 5/2007 | Iversen et al. | |
| 7,618,159 | B2 * | 11/2009 | Tamburrino et al. | 362/321 |
| 7,737,194 | B2 | 6/2010 | Kashiwagi et al. | |
| 7,847,302 | B2 | 12/2010 | Basin et al. | |
| 2005/0117327 | A1 | 6/2005 | Gupta | |
| 2005/0243558 | A1 | 11/2005 | Van Duyn | |
| 2006/0285316 | A1 | 12/2006 | Tufenkjian et al. | |
| 2007/0097703 | A1 | 5/2007 | Goldfain | |
| 2009/0161348 | A1 * | 6/2009 | Spartano et al. | 362/105 |
| 2009/0207617 | A1 | 8/2009 | Merchant et al. | |
| 2012/0120635 | A1 | 5/2012 | Strong et al. | |
| 2013/0141920 | A1 * | 6/2013 | Emerson et al. | 362/311.01 |

* cited by examiner

MEDICAL HEADLAMP OPTICAL ARRANGEMENT PERMITTING VARIABLE BEAM WIDTH

RELATED APPLICATIONS

This application is a continuation-in-part of application Ser. No. 13/972,489, filed Aug. 21, 2013, which in turn claims priority from provisional application Ser. No. 61/822,493, filed May 13, 2013. Both of the above noted applications are hereby incorporated by reference as if fully set forth herein.

BACKGROUND

A medical headlamp assembly is a critical part of the surgeon's suite of tools, as it is of great importance that a surgeon can clearly see in the operating theater. The ideal headlamp would be easily portable, light and comfortable to wear for at least four hours. Further, it would have battery power, mounted on the head strap, sufficient to last four hours from one charge, thereby eliminating the necessity of waist mounted battery pack and cables connecting this pack to the lamp, which are uncomfortable and complicate antiseptic protocol. Further the ideal headlamp assembly would create a bright beam of light that was homogenous and uniform in brightness and color, from edge-to-edge, directly along the surgeon's line of sight, without obscuring his or her line of sight. Also, it would be entirely silent, easily adjustable in position and would not be susceptible to infection by mold or any other sort of organism.

Unfortunately, these criteria are not only difficult to meet, but are also frequently at odds with each other. For example, although it is better to have a bright light, this creates more heat, which must be safely expressed from the lamp. It is helpful in the elimination of heat to make the lamp bigger, but doing so is likely to cause it to obscure the surgeon's line of sight and add unbearable weight. Another option for expressing heat would be to provide a fan, but this creates a sound, which may be difficult for the surgeon to tolerate. To permit longer battery life it would be helpful to have higher capacity batteries, but doing so makes the assembly heavier and more difficult for the surgeon to tolerate for a long period of time. The batteries could be placed in a waist pack, but doing so requires an electrical line extending from an aseptic area, about the waist underneath the scrubs (anything under the neck is a "sterile" area), to a non-sterile area, on the surgeon's head. This arrangement complicates aseptic protocol.

There is a currently available headlamp assembly that mounts batteries on the headband and that has batteries that can be swapped out, one at a time, for extended surgical periods. The light produced by this headlamp is on the order of 166 lumens in intensity. For many types of surgery, for example where a deep cavity that has been opened up inside a patient requires illumination, a higher intensity lamp is desirable.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other improvements.

In a first separate aspect, the present invention may take the form of a medical headlamp having a front surface from which a lamp light beam is emitted. The headlamp has a high efficiency light source producing a beam having a 3 dB beam width of greater than 100° and an annular light block, defining an annulus and placed immediately in front of the high efficiency light source, a light beam extending from the light block. Also, an optical assembly is positioned to receive light from the high efficiency light source assembly and produce a lamp light beam emitted from the front surface of the lamp. Further, a housing supports the light source and the optical assembly and an electrical conductor connects to the light source, for supplying electricity to the light source. Finally, the optical assembly includes an adjustable iris assembly including a user accessible actuator and an iris that is adjustable by the actuator, to be retracted away, thus leaving unaffected the light beam from the light block, or to be tightened to block a portion of the light beam from the annular light block, thus producing a thinner lamp light beam.

In a second separate aspect, the present invention may take the form of a medical headlamp having a front from which light is selectively emitted. The headlamp includes a beam origination portion that produces a light beam and an iris assembly, positioned in front of the beam origination portion, having a user accessible actuator and an iris, responsive to the actuator to block a user selectable portion of the light beam. The iris is also responsive to the actuator to block none of the light beam, for maximum efficiency, when a user so selects.

In a third separate aspect, the present invention may take the form of a lamp having a front from which light is selectively emitted. The lamp includes a beam origination portion, which produces a light beam and a beam modification portion, which can be controlled to block a selectable portion of the light beam and can also be controlled to block none of the light beam, for maximum efficiency. Further, when the beam modification portion is controlled to block none of the light beam, the lamp produces a beam of more than 90 lumens per watt of electrical power delivered to the lamp.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein be considered illustrative rather than restrictive.

DETAILED DESCRIPTION OF THE PREFERRED EMBODIMENTS

Definitions

For the purposes of this application, a "high efficiency light source" is an electrically powered light source having a light emitting surface area of less than 50 mm$^2$ that produces light at a rate of greater than 50 lumens per watt of input power and at a rate greater than 30 lumens per square millimeter of light emitting area. This term does not include packaging or a lens. If these items are included the phrase used is "high efficiency light source assembly".

A light emitting diode (LED), as used in the application, refers to a solid-state electrical device and does not include any lens or packaging. Others sometimes refer to this element as a "die," A light emitting diode assembly, includes packaging and a lens.

The term "most" as used in this application, means more than 50%.

The term "light" as used in this application refers to visible light.

The "front" of the medical lamp is the side from which light is emitted. The "longitudinal dimension" extends from front to back.

Figure 1:
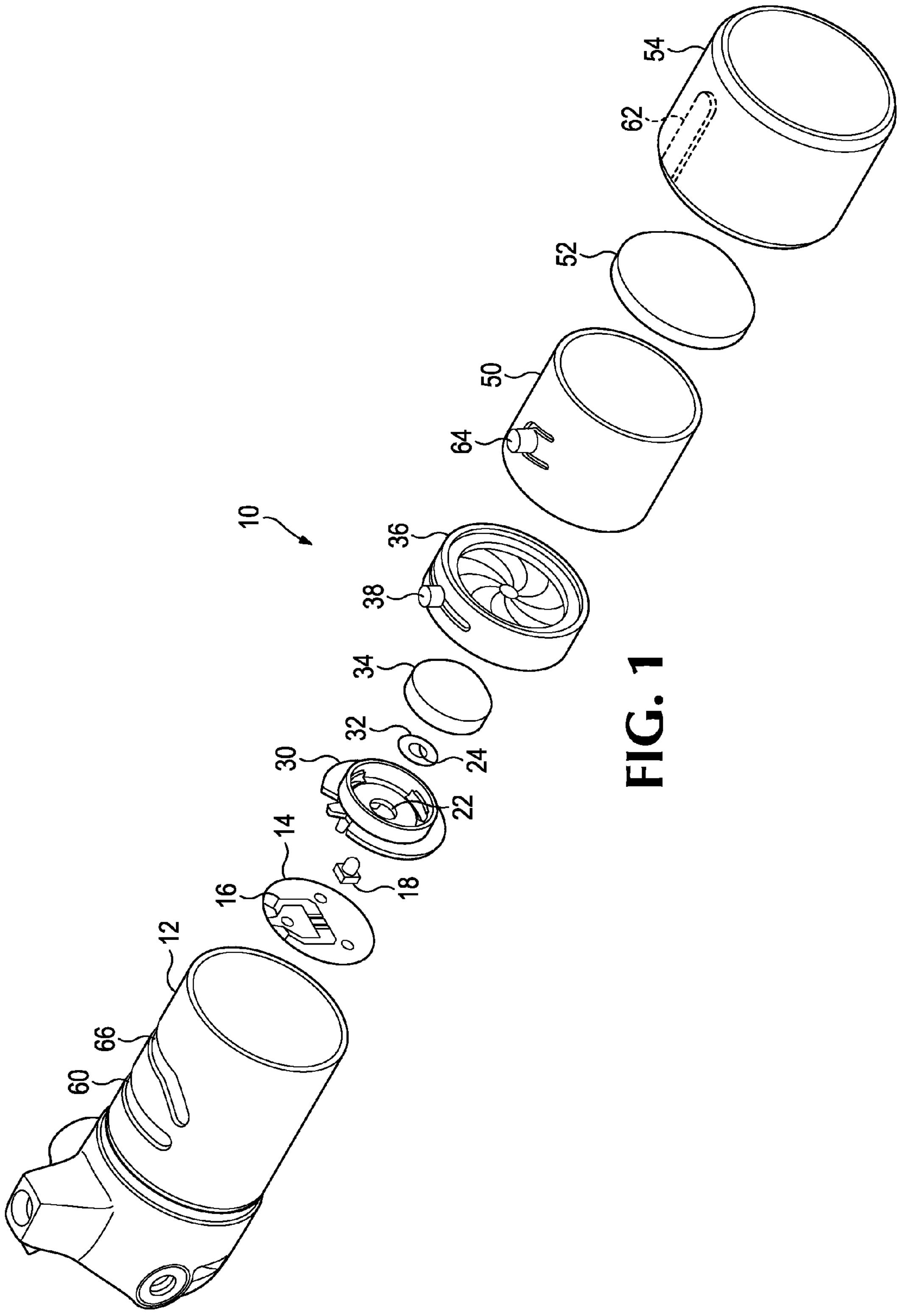
FIG. 1 shows an exploded view of a medical headlamp, according to the present invention.
Figure 2:
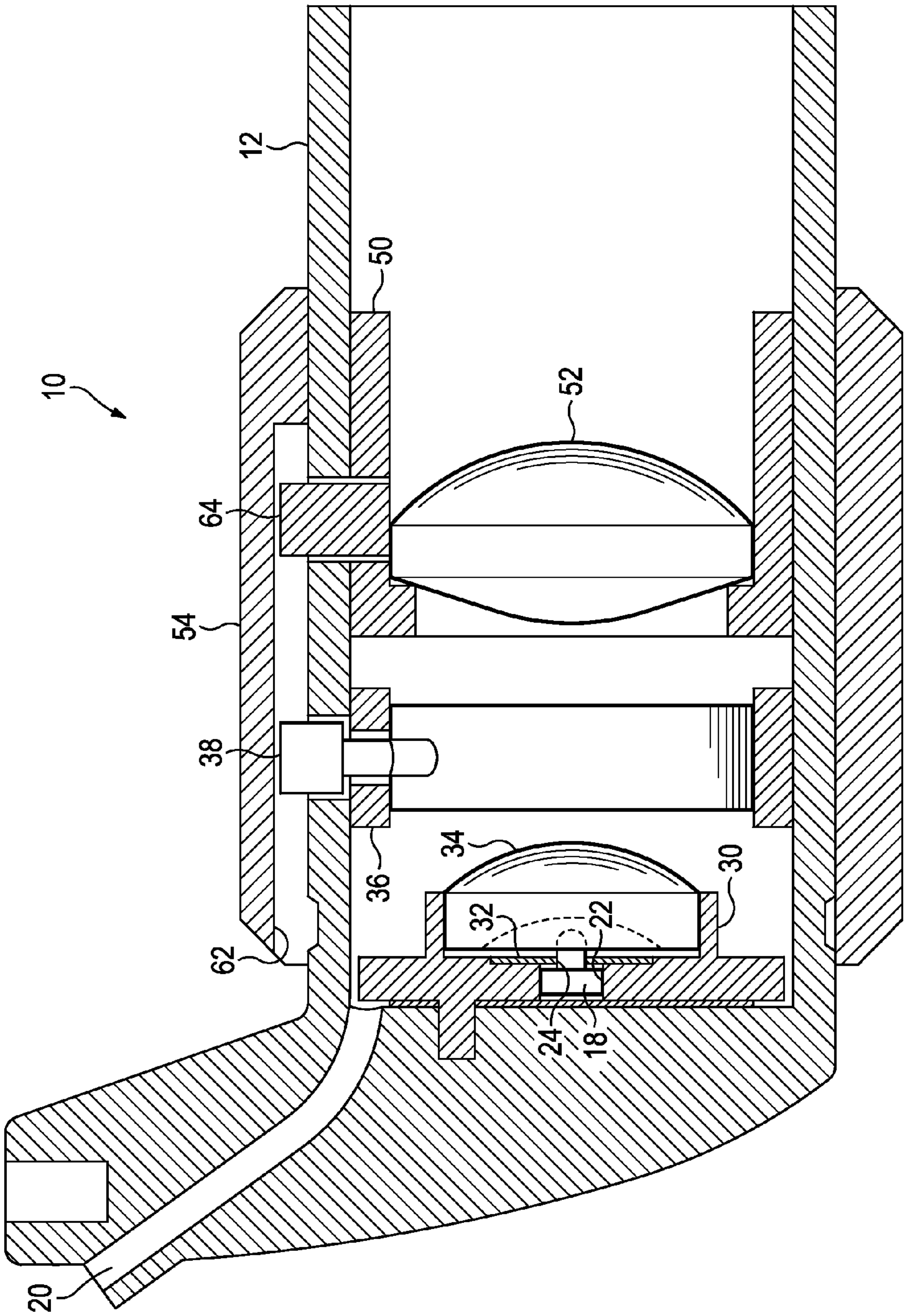
FIG. 2 shows a sectional view of the medical headlamp of FIG. 1.

The term "headlamp" is used to refer to the entire lamp or illuminating assembly, as shown in FIGS. 1 and 2, but not the headband (which may also be referred as "head strap") or the linkage, which together with headlamp form a headlamp assembly.

Referring to FIGS. 1 and 2, a high-efficiency medical headlamp 10 is shown, of the type that could be attached to a head strap assembly and used by a surgeon to light the surgical theater, or by a medical professional, in general, to illuminate an area of interest. This headlamp 10 is very efficient, producing a relatively high volume of light for the amount of electrical power consumed, thereby permitting the use of batteries mounted on the headband assembly, as opposed to mounted on a waist pack, with electrical cabling connecting the battery to the lights.

The headlamp 10 includes an aft barrel 12, which houses a round piece of flex circuit 14, upon which are defined conductive traces 16, adapted to drive a light emitting diode (LED) assembly 18, more generally termed "a high efficiency light assembly." Aft barrel 12 defines a channel 20 (FIG. 2) for an electrical wire to pass through, to connect a supply of electricity to traces 16.

A portion of LED assembly 18 extends through an aperture 22 in a prime lens holder 30, and also extends through an aperture 24 in an annular light block 32, which has a thickness on the order of 25 μm and which blocks the peripheral light produced by assembly 18, thereby creating a crisp outline for the spot of light produced by headlamp 10. In front of and surrounding the portion of the high efficiency light source 18 that protrudes through aperture 24 is a prime lens 34 having a convex rear surface (FIG. 2). Immediately in front of prime lens 34 an iris 36 acts to permit an adjustment by actuator 38, to create a thinner light beam, which will be described in more depth, below. In front of iris 36 is an exit lens holder 50, containing an exit lens 52. An outer ring 54 surrounds exit lens holder 50.

The iris actuator 38 fits through a circumferential groove 60 defined in aft barrel 12 and further extends into straight forward and backward groove 62, defined in outer ring 54. Similarly, a groove follower 64 on exit lens holder 50 protrudes through a groove 66 on aft barrel, and also extends into groove 62 in outer ring 54. The result of this arrangement is that as outer ring 54 is rotated, both actuator 38 and groove follower 64 are moved circumferentially. In addition, over part of the travel of outer ring 54, groove follower 64 is moved forward or backward, as slot 66 is diagonal. This changes the focus of the light beam produced by headlamp 10. Over the remainder of the travel of outer ring 54, groove follower 64 is only moved circumferentially, which has no effect on the optical characteristics of headlamp 10.

Figure 3:
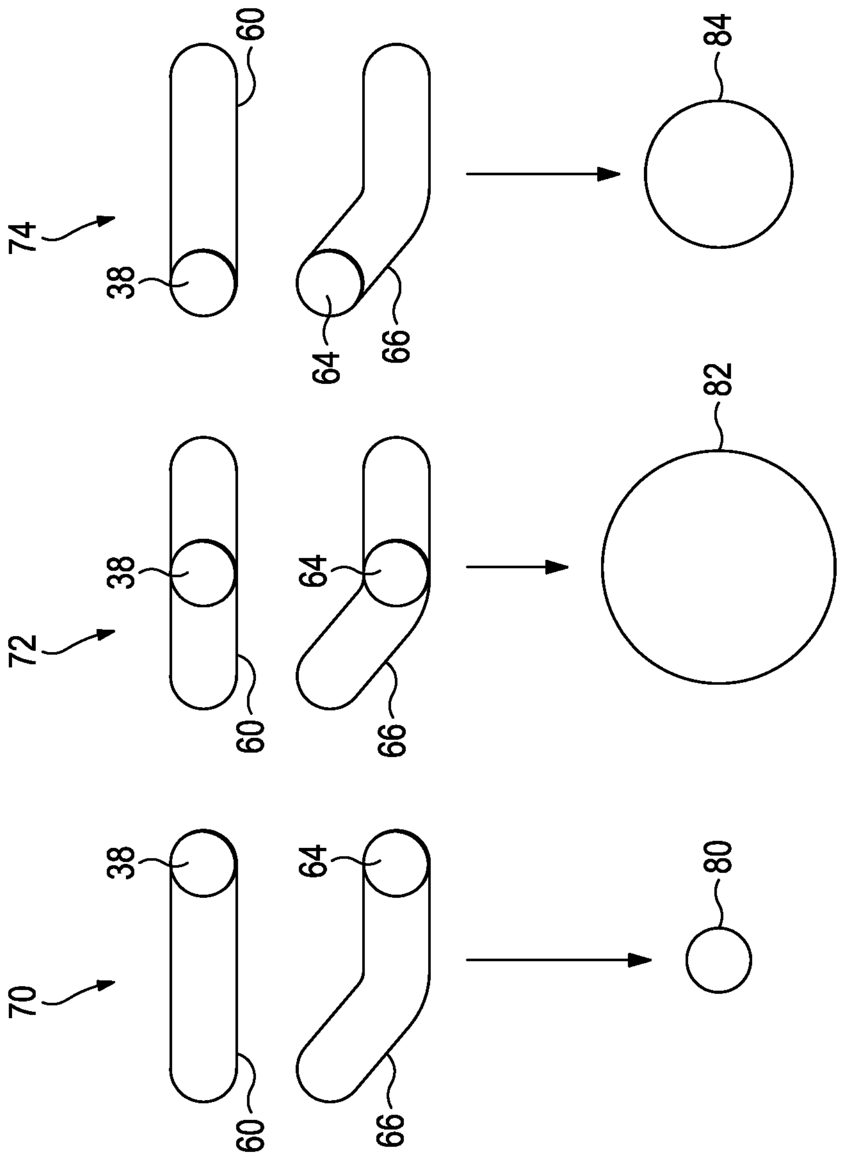
FIG. 3 is an illustration of the effect of the barrel adjustment on the light beam diameter.

Referring to FIG. 3, in configuration 70 outer ring is at the clockwise end of its travel, which causes actuator 38 to be at the extreme right end of groove 60 (from the perspective of an observer looking at groove 60). This causes iris 36 to be in its narrowest aperture state, creating a very thin light beam 80. Groove follower 64 is also at the extreme right hand side of groove 66, causing exit lens 52 to be at the extreme far forward extent of its range of motion. This option is sometimes required, particularly by ear, nose and throat specialists. In configuration 72, both actuator 38 and follower 64 are at the mid-range of their circumferential motion. This increases the aperture defined by iris 36 enough so that the beam width is defined by annular light block 24. At the same time, exit lens is maintained in its far forward position, defocusing the beam to create a wider, although less well focused light spot 82. Finally, in configuration 74, the actuator 38 and follower 64 are at the extreme left hand extent of their travel, causing iris to be definitively not affecting the beam 84, which is shaped entirely by annular light block 24. The exit lens 52, however, is brought back in to create a tight, well-focused beam with sharp boundaries. Accordingly, a full range of beam widths are permitted, while removing the iris entirely from engagement with the light beam for the wide beam geometries, thereby resulting in a more efficient system, when it is needed most, for the illumination of deep cavity surgery.

The placement of the light block 32 together with its 25 μm thickness, creates a sharp boundary about the light, and ultimately creates a crisp spot of light, at the typical 80-100 mm (16-18 in) working distance. Table 1 shows the characteristics of LED assembly 18 for four differing embodiments. In an alternative preferred embodiment an LED assembly is used that is similar to the Oslon Square LED assembly, but includes more than one LED die, and in another preferred embodiment more than one LED assembly is used.

TABLE 1

LED Assemblies Used in Various Embodiments

| | Manufacturer Designation | Further Designation Class (Color) | LED Beam Angle |
|---|---|---|---|
| LED Assembly of Emb. 1 | Oslon Square | PC | 120 |
| LED Assembly of Emb. 2 | Oslon Square | EC | 120 |
| LED Assembly of Emb. 3 | Oslon Square | CC | 120 |
| LED Assembly of Emb. 4 | Oslon Square | EQW | 120 |

| | Lumen Output | | | |
|---|---|---|---|---|
| Current Applied | 750 mA | 1 A | 1.2 A | 1.5 A |

TABLE 1-continued

| LED Assemblies Used in Various Embodiments | | | | |
|---|---|---|---|---|
| LED Assembly of Emb. 1 | 252-346 | 312-429 | 372-511 | 408-561 |
| LED Assembly of Emb. 2 | 220-294 | 273-364 | 325-434 | 357-476 |
| LED Assembly of Emb. 3 | 189-271 | 234-336 | 279-401 | 306-440 |
| LED Assembly of Emb. 4 | 294-409 | 364-507 | 434-604 | 476-663 |
| | Voltage | | | |
| Current Applied | 750 mA | 1 A | 1.2 A | 1.5 A |
| LED Assembly of Emb. 1 | 3.08 | 3.15 | 3.2 | 3.28 |
| LED Assembly of Emb. 2 | 3.08 | 3.15 | 3.2 | 3.28 |
| LED Assembly of Emb. 3 | 3.08 | 3.15 | 3.2 | 3.28 |
| LED Assembly of Emb. 4 | 3.08 | 3.15 | 3.2 | 3.28 |
| | Wattage | | | |
| Current Applied | 750 mA | 1 A | 1.2 A | 1.5 A |
| LED Assembly of Emb. 1 | 2.31 | 3.15 | 3.84 | 4.92 |
| LED Assembly of Emb. 2 | 2.31 | 3.15 | 3.84 | 4.92 |
| LED Assembly of Emb. 3 | 2.31 | 3.15 | 3.84 | 4.92 |
| LED Assembly of Emb. 4 | 2.31 | 3.15 | 3.84 | 4.92 |
| | Lm/Watt @ max lm | | | |
| Current Applied | 750 mA | 1 A | 1.2 A | 1.5 A |
| LED Assembly of Emb. 1 | 150 | 136 | 133 | 114 |
| LED Assembly of Emb. 2 | 127 | 116 | 113 | 97 |
| LED Assembly of Emb. 3 | 117 | 107 | 104 | 89 |
| LED Assembly of Emb. 4 | 177 | 161 | 157 | 135 |

Figure 4:
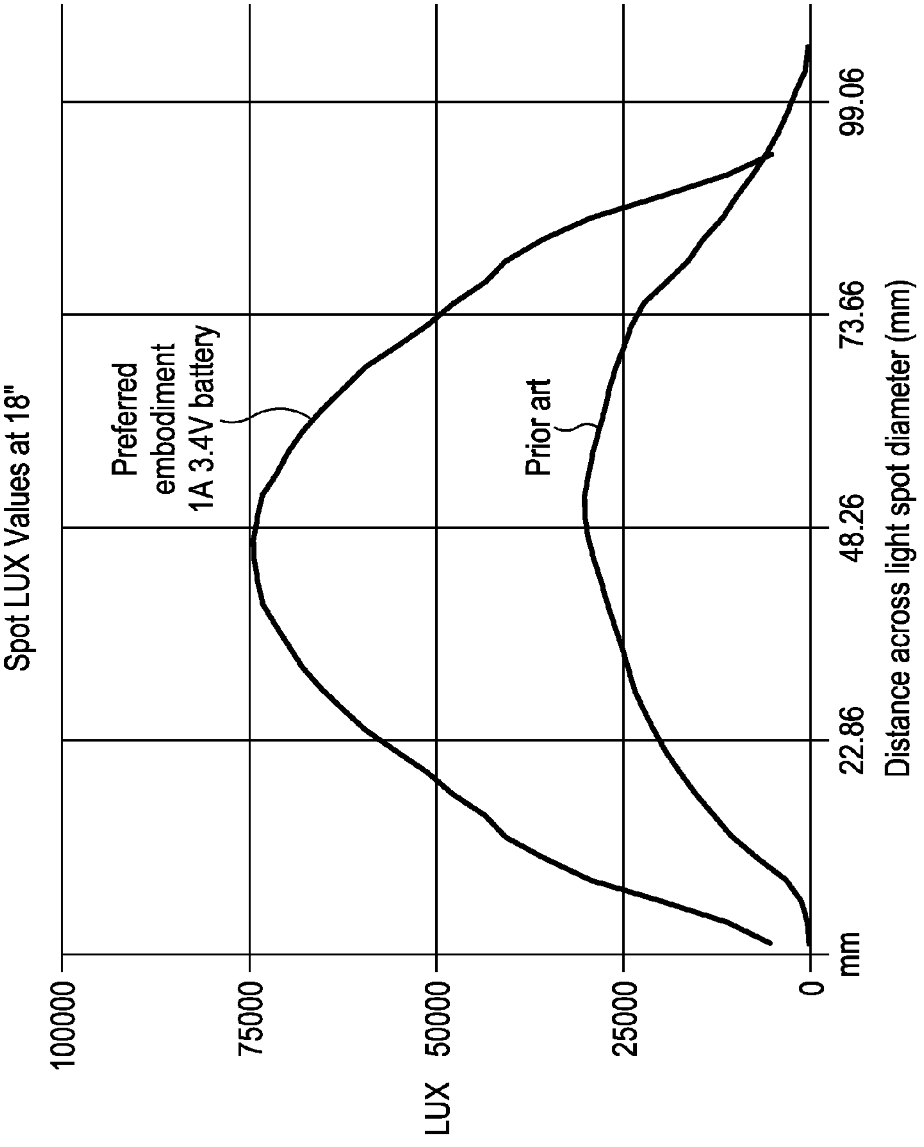
FIG. 4 is a graph of the intensity of a light spot created by a preferred embodiment of a headlamp, as described herein.

The effect of the above detailed design is a medical headlamp 10, that can be incorporated into an assembly with batteries mounted on the head strap assembly, and without a fan to provide forced air cooling, but which produces a brighter beam than previously available headlamp assemblies of this sort. The beam produced, in one preferred embodiment, has a light volume of 413 lumens with a color rendering index of at least 65. The beam is emitted relatively evenly from the 23 mm diameter front surfaces of the exit lens 52, and spreads out by 4.19 degrees in all directions as the beam advances. Referring to FIG. 4, a one (1) Amp lamp, as described above, where the voltage drop from the batteries is 3.4 Volts, produces a spot of light at 45.7 cm graph in FIG. 4 says mm (18 inches) as shown. With a bright central area, about 52 mm wide at all above 50,000 lux at a color rendering index (CRI) of greater than 65. A ring of about 10 mm width surrounds this, where the light intensity declines from 50,000 lux to 25,000 lux. At the edges of the light beam, the brightness drops off by 20 dB in 0.5°. The lamp is operable in an ambient temperature of up to 30° Celsius, with no fan to cool the lamp.

When iris 36 is opened up so that it does not block any of the light from LED 18, the proportion of this light that is emitted in the light beam from the exit lens 52 is greater than in prior art systems. This is because: 1) the distance between the LED assembly 18 and the prime lens 34 is shortened to virtually nothing, as the LED assembly 18 protrudes into a concavity in the prime lens 34; 2) the annular light block 32 sits on the lens of the LED assembly 18, sufficiently far back that it blocks only a small proportion of the light. In one preferred embodiment, 70% of the light produced by LED assembly 18 is emitted from the exit lens 52 as a light beam. Alternative preferred embodiments emit anywhere from 50% to 70% of the light produced by the LED assembly 18 out of exit lens 52. This compares favorably with prior art systems where less than 45% of the light produced by the light source is emitted in the beam. In a preferred embodiment the light beam produced from exit lens 52 has a volume of 114 to 161 lumens for every watt of power applied to LED assembly 18. In one alternative preferred embodiment this figure ranges from 90 lumens of output light per watt to 161 lumens of output light per watt. Many prior art systems include an iris but do not include any part analogous to light block 32, so that the iris is always blocking a portion of the light beam produced by the light source. Incorporating both the annular light block 32 and the iris 36, makes it possible to create a very high intensity beam, with minimum battery drain when the iris is opened up wide enough so that it blocks no light, but also to have a thin beam, when warranted.

This device greatly eases the task of the surgeon, who may now have an adequately bright and wide spot light beam for deep cavity surgery, without the need for the distracting noise and cumbersome extra weight of a fan and without the need of any power cable traversing from a sterile to a non-sterile zone. The same lamp may, in its narrow beam state of adjustment, be used by an ear, nose and throat specialist.

While a number of exemplary aspects and embodiments have been discussed above, those possessed of skill in the art will recognize certain modifications, permutations, additions, and sub-combinations thereof. It is therefore intended that the following appended claims and claims hereafter introduced are interpreted to include all such modifications, permutations, additions and sub-combinations as are within their true spirit and scope.

The invention claimed is:

1. A medical headlamp having a front surface from which a lamp light beam is emitted, comprising:

(a) a high efficiency light source producing a light beam;

(b) an annular light block, defining an annulus and placed immediately in front of said high efficiency light source to block a peripheral portion of said light beam, thereby creating a crisp-boundary light beam extending from said light block;

(c) an optical assembly, including a prime lens and an exit lens and positioned to receive light from said high efficiency light source and produce a lamp light beam emitted from said front surface of said lamp;

(d) a housing supporting said light source and said optical assembly and an electrical conductor connected to said light source, for supplying electricity to said light source; and (e) wherein said optical assembly includes an adjustable iris assembly in front of said annular light block and including a user accessible actuator and an iris that is adjustable by said actuator, either to be retracted, thus leaving unaffected said crisp-boundary light beam from said light block, or to be tightened to block a portion of said crisp-boundary light beam from said annular light block, thus producing a thinner lamp light beam, said user adjustable actuator having a range of motion and said exit lens being moved backward or forward in response to said user accessible actuator, over at least a portion of said actuator's range of motion and wherein a portion of said actuator's range of motion moves said iris to block a variable portion of said light beam from said light block, and over said portion of said actuator's range said exit lens is not moved.

2. The medical headlamp of claim 1, wherein said high efficiency light source is a light emitting diode.

3. The medical headlamp of claim 1, wherein a portion of said actuator's range of motion moves said iris over a range that does not block said light beam from said light block, and over said portion of said actuator's range said exit lens is moved forward or backward by said actuator.

4. The medical headlamp of claim 1, wherein when said iris is expanded to leave said light beam unaffected, said headlamp light beam has a circular edge wherein light intensity decreases by 20 dB over 0.5° from a position inside said headlamp light beam to a position outside said headlamp light beam.

* * * * *